(12) United States Patent
El-Sawy et al.

(10) Patent No.: US 8,986,751 B2
(45) Date of Patent: Mar. 24, 2015

(54) MEDICINAL OROBANCHEACE EXTRACTS

(71) Applicant: Pharco Pharmaceuticals, Alexandria (EG)

(72) Inventors: Mohamed Fakhr El-Din El-Sawy, Alexandria (EG); Sherine Hassan Abbas Helmy, Alexandria (EG); Layla M. F. El-Din El-Sawy, Alexandria (EG); Maha Adel El Demellawy, Alexandria (EG); Shefaa M. F. El-Sawy, Alexandria (EG)

( * ) Notice: Subject to any disclaimer, the term of this patent is extended or adjusted under 35 U.S.C. 154(b) by 96 days.

(21) Appl. No.: 13/872,699

(22) Filed: Apr. 29, 2013

(65) Prior Publication Data

US 2013/0243890 A1 Sep. 19, 2013

Related U.S. Application Data

(63) Continuation-in-part of application No. PCT/EG2011/000023, filed on Oct. 25, 2011.

(30) Foreign Application Priority Data

Apr. 17, 2011 (EG) .................. 2011040596

(51) Int. Cl.
*A61K 36/00* (2006.01)
*A61K 36/64* (2006.01)
*A61J 3/00* (2006.01)

(52) U.S. Cl.
CPC ... *A61K 36/64* (2013.01); *A61J 3/00* (2013.01)
USPC .......................................... 424/725

(58) Field of Classification Search
None
See application file for complete search history.

(56) References Cited

U.S. PATENT DOCUMENTS 5,989,556 A 11/1999 Tsai et al.

FOREIGN PATENT DOCUMENTS

| CN | 101411753 | | 4/2009 |
| CN | 101411753 A | * | 4/2009 |
| JP | 2009057340 | | 3/2009 |
| JP | 2009196905 | | 9/2009 |
| WO | WO/92/16544 | | 10/1992 |
| WO | PCT/EG2011/000023 | | 10/2011 |

OTHER PUBLICATIONS

Davis, G. Treatment of Chronic Hepatitis C; British Medical Journal; Nov. 17, 2001; 323, 7322; ProQuest Central, pp. 1141-1142.*
Hussain et al. New Hepatitic C IRUS Drug Discovery Strategies and Model Systems; Expert Opin. Drug Discov. (2012) 7(9), pp. 849-859.*
Phillipson, J. New Drugs From Nature—It Could Be Yew; Phytotherapy Research 13 (1999) pp. 2-8.*
Raskin et al. Can an Apple a Day Keep the Doctor Away? Current Pharmaceutical Design, 2004, 10, 3419-3429.*
Revilla et al. Comparison of Several Procedures used for the Extraction of Anthocynains From Red Grapes; J. Agric. Food Chem. 1998, 46, pp. 4592-4597.*
Sharma, PK: Direct Uses of Medicinal Plants and Their Identification; Sarup & Sons Publishing, Delhi, India, 2008; p. 252.*
El-Hawash SA, Abdel Wahab AE, El-Demellawy MA, "Cyanoacetic Acid Hydrazones of 3-(and 4-) Acetylpyridine and Some Derived Ring Systems as Potential Anti-tumor and Anti-HCV Agents," Arch Pharm (Weinheim), (2006), 339:14-23.
Quan J, Yin X, Xu H, "*Boschniakia rossica* prevents the carbon tetrachloride-induced hepatotoxicity in rat". Experimental and Toxicologic Pathology. Jena. De. (Jan. 1, 2011), vol. 63, No. 1-2, pp. 53-59.
Ghosh Nilanjan et al: "Recent advances in herbal medicine for treatment of liver diseases". Pharmaceutical Biology. Swets and Zeitlinger. Lisse. NL. (Sep. 1, 2011), vol. 49, No. 9, pp. 970-988.
Azzam H S et al: "Natural products and chronic hepatitis C virus". Liver International. Blackwell Munksgaard. Oxford. GB. (Feb. 1, 2007). vol. 27, No. 1, pp. 17-25.
Masato Tsuchiya et al: "Protective effect of Juzen-taiho-to on hepatocarcinogenesis is mediated through the inhibition of Kupffer cell-induced oxidative stress". International Journal of Cancer. (Dec. 1, 2008). vol. 123, No. 11, pp. 2503-2511.

* cited by examiner

*Primary Examiner* — Patricia A Leith
(74) *Attorney, Agent, or Firm* — Boulware & Valoir (57) ABSTRACT

Pharmaceutical extracts from Egyptian broomrape have proven efficacy against HCV and NAFLD. Compositions and method of making and using same are provided.

1 Claim, 1 Drawing Sheet

(Prior Art)

MEDICINAL OROBANCHEACE EXTRACTS

PRIOR RELATED APPLICATIONS

This application is a continuation-in-part of WO/2012/143017, filed on Oct. 25, 2011, which claims priority to Egyptian Application 2011040596, filed on Apr. 17, 2011 both are incorporated by reference in their entirety herein.

FIELD OF THE DISCLOSURE

The disclosure generally relates to methods and compositions for treating hepatitis C virus (HCV) and non-alcoholic fatty acid liver disease (NAFLD), as well as method of making such compositions.

BACKGROUND OF THE DISCLOSURE

Orobanchaceae—the Broomrape—is a family of flowering plants of the order Lamiales, with about 90 genera and more than 2000 species, many of which genera were formerly included in the family Scrophulariaceae sensu lato. Together they are a monophyletic group, forming a distinct family, found mainly in temperate Eurasia, North America, South America, parts of Australia, New Zealand, and tropical Africa.

The Orobanchaceae are annual herbs or perennial herbs or shrubs, and all (except *Lindenbergia* and *Rehmannia*) are parasitic on the roots of other plants—either holoparasitic or hemiparasitic (fully or partly parasitic). The holoparasitic species completely lack chlorophyll and therefore cannot perform photosynthesis. They may be yellowish, brownish, purplish, or white. Their alternate leaves have been reduced to somewhat fleshy, sessile scales. The hemiparasitic species (transferred from *Scrophulariaceae*) are capable of photosynthesis, and may be either facultative or obligate parasites.

Naked Broomrape was used historically by some North American tribes for externally treating ulcers and cancerous growths, and internally for treating some bowel disorders. California Broomrape or cancer root is used externally to treat skin infections caused by *Streptococcus*, as a poultice or wash for wounds, ulcers and herpes lesions. Ancient Chinese herbalists have also used Broomrape varieties for various ailments. For example, *Orobanche cumana* is said to have the effects of antifatigue, facilitating immune function and an andrin-like action.

However, this family is mostly famous in a negative way. It is widely scourged for the tremendous damage to crops caused by some species in the genera *Orobanche* and *Striga*.

To date, broomrape extracts have never been used to treat HCV or NAFLD.

SUMMARY OF THE DISCLOSURE

Pharmaceutical compounds have been extracted from a member of the family Orobancheace and have been proven to have an effect against HCV infected cells and induced non-alcoholic fatty liver in laboratory models.

Figure 1:
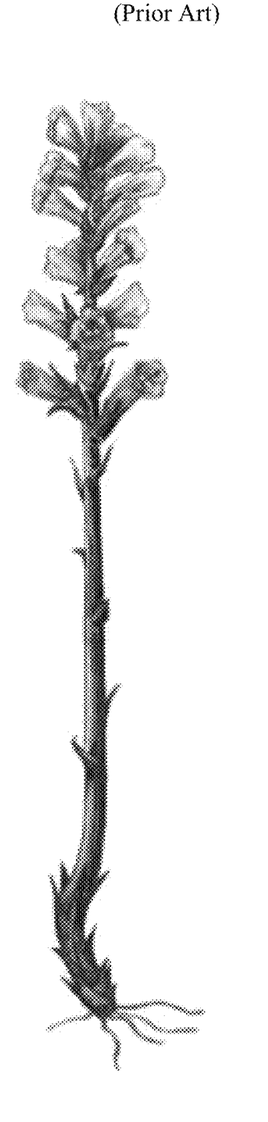
FIG. 1 is an illustration of the Egyptian broomrape (prior art).

The plant is identified as a member of the family Orobancheace, species *aegyptiaca*. *Orobanche aegyptiaca* is a species of Broomrape, commonly known as Egyptian Broomrape, and is a obligate parasite of a variety of vegetable and some ornamental species. Shown in FIG. 1, the stem is about 15-50 cm, usually branched, yellowish, up to 6-8 mm thick in its midsection, with slight thickening at base, and with some ovoid-lanceolate scales up to 15 mm length. One plant produces over 1 million seeds every year. The seeds maintain their germinating capacity in soil for a long time under favorable conditions. The parasite prefers cultivated (rarely wild-growing) plants of more than 90 species in different families of flower plants (except monocotyledons).

This species is found in the lower Volga, Crimea, the Caucasus, Central Asia (in the former USSR), the eastern Mediterranean, Central Asia and Asia Minor.

The parasite occurs in fields, in watermelon plantations, in wild-growing plants, usually near roads and along field edges, but is rarely seen on stony slopes. It is the most dangerous parasite of all Broomrape species, parasitizing melons, cucumbers, watermelons, pumpkins, tomatoes, red pepper, eggplants, potatoes, maize, tobacco, groundnut, and, though more rarely, sunflowers, cabbage, mustard, radish, carrots, and sesame.

Generally, the extraction method is as follows:

1) Dried powdered whole plant is mixed with 10-20 fold of sterile extraction solution, which can be water or any aqueous buffer solution, plus or minus detergents, and the like.

2) The mixture is heated to a boil under 1-2 kilo Pascal pressure for 10-20 minutes.

3) The liquid extract is collected, filtered if necessary, and then lyophilized.

4) Different concentrations of the lyophilized extract were then tested against lab cultured HCV replication and progression using published methodology.

Other extraction methods can be employed, as suitable for water soluble components. For example, such methods include supercritical $CO_2$ extraction, steam extraction, aqueous two-phase systems, and the like. If desired, the dried plant can first be lysed before extract, e.g., by grinding, organic lysis, enzymatic lysis of plant cell walls, or can be physically lysed by freezing and thawing before extraction, and the like. Defatting procedures can also precede aqueous extraction, for example, the material can be defatted with petroleum ether or methanol/chloroform, and the like.

Furthermore, crude aqueous extracts can be further purified, for example, by size exclusion chromatography, ion exchange chromatography, HPLC, precipitation, crystallization, and the like.

The crude extract has proven its efficacy in an induced nonalcoholic fatty liver in animal model, as well as ex vivo activity against HCV in PCMB cells.

The active ingredient or ingredients of the aqueous extract of the plant material can combined with other active ingredients, but preferably are used alone. The active ingredient or ingredients of the aqueous extract of plant material can be used as is, or can be formulated with known pharmaceutically acceptable carriers, diluents and/or excipients For example, gelatin capsules containing dried aqueous extract can be produced containing a suitable dose of the active ingredient(s). Optionally, packets containing the dried extract can be provided for mixture with e.g., hot fluids, to be taken orally. The extract can also be formulated with solid carriers for pressing into pill forms, especially with delayed release excipients for formulating once a day pill forms.

It may also be possible to prepare forms of the active ingredients suitable for non-oral routes of administration, such as inhalational, buccal, sublingual, nasal, suppository or parenteral dosage forms.

We also used TLC and HPLC to further purify the active ingredient(s) to be further studied and to determine their efficacy, although this work is ongoing. The different compounds and their structure both are being analyzed and determined. Meanwhile, the primary compounds being identified are glycosylated compounds of natural origin.

This aqueous extract has been fractioned by HPLC producing 10 different fractions that are tested for their anti-HCV efficacy. For the steatohepatitis (also known as fatty liver disease) the total lyophilized extract was used for the treatment. It is proposed that the extract contains compounds that bind with the virus and preventing its cellular entry and contains a fatty acid or protein that may engulf and coat the genomic material (positive strand RNA) of the virus preventing its antisense synthesis.

Both tests for the anti-steatohepatitis and anti-HCV efficacy were executed and proven to be efficacious. HPLC fractions are being retested currently for the treatment of HCV.

In more detail, the invention may comprise one or more of the following: A composition comprising an aqueous extract of Orobanche aegyptiaca together with a pharmaceutically acceptable carrier; a method of treating hepatitis C virus (HCV), comprising administering an effective amount of the composition of claim 1 to a patient with HCV; a method of treating non-alcoholic fatty acid liver disease (NAFLD), comprising administering an effective amount of the composition described to a patient with NAFLD; a method of preparing the pharmaceutical composition described, said method comprising comminutting a Orobanche aegyptiaca, extracting a water soluble component from said comminuted Orobanche aegyptiaca and adding a pharmaceutically acceptable carrier to said water soluble component; a method of preparing the pharmaceutical composition herein, said method comprising comminutting a Orobanche aegyptiaca, extracting a water soluble component from said comminuted whole plant, lyophilizing said water soluble component; and adding a pharmaceutically acceptable carrier to said lyophilized water soluble component.

The term "plant material," as used herein, refers to any part or parts of a plant taken either individually or in a group. Examples include, but are not limited to, leaves, flowers, roots, seeds, stems, rhizomes, tubers, and other parts of a plant, including those plants described herein as potential plant species of the invention. Preferred plant material herein includes the stem.

The term "aqueous extract," as used herein, refers to a composition prepared by contacting plant material with an aqueous solvent following standard procedures such as those described herein. The term encompasses crude extracts, prepared by a simple aqueous extraction, as well as crude extracts that have been subjected to one or more separation and/or purification steps, including substantially purified and purified active ingredient(s) and concentrates or fractions derived from a crude extract by subjecting the crude extract to one or more additional extraction, concentration, fractionation, filtration, condensation, distillation or other purification step. The plant extract may be in liquid form, such as a solution, concentrate or distillate, semiliquid form, such as a gel or paste, or it may be in solid form, such as in granulate or powder form.

The term "active ingredient" includes one or more active ingredients (e.g., compounds having pharmaceutically efficacy against at least HCV and NAFALD, and possibly other diseases) isolatable from at least the Egyptian broomrape, and potentially from other broomrape species or even other plant families. It includes both synthetic (chemically made) and natural (derived from plants) forms of the active ingredient.

The term "isolated," when used in reference to a compound or compounds having pharmaceutical activity, refers to a form of the active ingredient that is relatively free of proteins, nucleic acids, lipids, cell wall, carbohydrates or other materials with which it is naturally associated in a live plant.

The term "substantially purified," when used in reference to an active ingredient, refers to a form of the active ingredient that is at least 75% pure when analyzed by HPLC.

The term "purified," when used in reference to an active ingredient refers to a form of the compound(s) that is at least 90% pure, and preferably is at least 95, 98 or 99% pure when analyzed by HPLC.

The terms "therapy," and "treatment," as used interchangeably herein, refer to an intervention performed with the intention of improving a recipient's medical status. The improvement can be subjective or objective and is related to the amelioration of the symptoms associated with, preventing the development of, or altering the pathology of a disease, disorder or condition being treated. Thus, the terms therapy and treatment are used in the broadest sense, and include the prevention (prophylaxis), moderation, reduction, and curing of a disease, disorder or condition at various stages. Prevention of deterioration of a recipient's status (i.e. stabilization of the disease, disorder or condition) is also encompassed by the terms. Those in need of therapy/treatment include those already having the disease, disorder or condition as well as those prone to, or at risk of developing, the disease, disorder or condition and those in whom the disease, disorder or condition is to be prevented.

The term "subject" or "patient," as used herein, refers to an animal in need of treatment. The term "animal," as used herein, refers to both human and non-human animals, including, but not limited to, mammals, birds and fish.

The term "nutraceutical," as used herein, refers to a food or dietary supplement that protects or promotes health and/or provides a benefit to a subject, which can affect the long term health of the subject. The term "phytoceutical," as used herein, refers to a plant-comprising composition having therapeutic properties.

The use of the word "a" or "an" when used in conjunction with the term "comprising" in the claims or the specification means one or more than one, unless the context dictates otherwise. The term "about" means the stated value plus or minus the margin of error of measurement or plus or minus 10% if no method of measurement is indicated. The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim. The phrase "consisting of" is closed, and excludes all additional elements. The phrase "consisting essentially of" excludes additional material elements, but allows the inclusions of non-material elements that do not substantially change the nature of the invention.

| ABBREVIATION | TERM |
| --- | --- |
| bw | Body weight |
| cDNA | complimentary DNA |
| DNA | Deoxyribonucleic acid |
| dNTPs | Deoxynucelotide triphosphates |
| FBS | Fetal bovine serum |
| HCV | Hepatitis C virus |
| PBMC | Peripheral blood mononuclear cell |
| PCR | Polymerase chain reaction |
| RNA | Ribonucleic acid |
| RPMI medium | Roswell Park Memorial Institute medium |
| RT-PCR | Real Time PCR |

DETAILED DESCRIPTION

The disclosure provides novel pharmaceutical extracts from broomrape and novel uses for same.

The present invention is exemplified with respect to *Orobanche aegyptiaca*. However, this species is exemplary only, and the invention can be broadly applied to other species of broomrape with similar active ingredients. Other suitable species may include Thistle Broomrape (*Orobanche reticulata*), Nodding Broomrape (*Orobanche cernua*) and Calceolaria (*Calceolaria serrata*).

The following examples are intended to be illustrative only, and not unduly limit the scope of the appended claims.

Wild Egyptian Broomrape EU2010-12

The preferred species is *Orobanche aegyptiaca*. Commonly known as "Egyptian Broomrape", it is an obligate holoparasite from the family Orobanchaceae with a complex life cycle. This parasite is most common in the Middle East and has a wide host range including many economically important crops.

When the seeds start to germinate, it puts out a root-like growth that attaches to the roots of nearby hosts. When a successful connection has been made with the host, the parasite can grow rapidly using water and nutrients taken from the host, causing yellowing of leaves, stunting and wilting of the host plant. After emergence the parasite will grow until it flowers, produces seed and dies. The complete cycle takes 10 to 15 weeks.

*Orobanche aegyptiaca* is an unconventional edible plant (similar to asparagus) that belongs to the local flora in Egypt and is readily consumed by many people. Thus, it appears to be relatively safe to ingest.

Plant Eu2010-12 was obtained by collection of several co-located specimens from Alexandria farm areas that has typical specimens of this species.

Aqueous Extracts

The fresh plant was collected, cleaned from other herbs and washed in fresh water, then sundried. Finally the dried plant was collected and stored in a dry dark place at room temperature. Dried plant was powdered by grinding and stored in dark and cold conditions before extraction.

A crude water extract was prepared by weighing 10-20 grams of the dried and ground plant in 100-150 mls of distilled water in a covered glass bottle in the autoclave at 121-125° C. for 20-30 minutes under pressure. The extract was then filtered, followed by freeze drying. The lyophilized extract was then sent to be fractioned by HPLC and the whole lyophilized powder was used to test for its safety and efficacy.

Toxocology and Safety Study

The herb used in this study was provided as 5 g powder sachets, by Prof. Dr. Mohammed Fakhr El-Din El-Sawy sponsored by European Egyptian Pharmaceutical Industries (EEPI), Alexandria, Egypt. This powder was prepared as described above, from the same species of broomrape. A stock solution from the dried plant was freshly prepared, by boiling 5 g from the dried plant at 100 ml distilled water for 2 minutes and filtered (equivalent to 80 ml), i.e. 5 g drug present in 80 ml filtrate.

Animal Methodology

For acute and chronic studies, the filtrate was given to the mice, rats, and rabbits by intra-gastric tubes and dogs by addition to its drinking water at these levels 0, 1.5 and 3 g/kg body weight. To estimate the dose level 1.5 g/kg body weight, each animal having a 100 g body weight received 2.4 ml from this filtrate plus 2.4 ml distilled water. While, to estimate the dose level at 3 g/kg each animal having a 100 g body weight received 4.8 ml from this filtrate. Control groups received only 4.8 ml distilled water.

These amounts (4.8 ml) for each animal divided equally and given twice daily (2.4 ml each time).

For carcinogenicity studies, the tested drug powder was given to the animals by its addition to their diets at different concentrations described in the methodology below.

Acute Toxicity Studies

This plant is an edible plant where people eat the stems and leaves as vegetable like asparagus, although it is not a commonly used vegetable. Therefore, it was acceptable to use it in a healthy volunteers pilot study. Also, it had been used to treat urinary tract infection in traditional folk medicine. The dose administered to the animals to test for the LD 50 (equivalent to 5 gm/kg body weight) was more than 30 times the recommended therapeutic human dose.

Acute toxicity studies were carried out in mice and rats. Single doses of the drug and the water as the vehicle at the same volumes were given orally by stomach tube to adult albino Swiss mice or rats. Clinical signs, symptoms and mortality were recorded during a 14-day observation period. The LD50 values were tested.

Doses were determined based on logarithmic doses as follows: The therapeutic dose suggested by the PI based on pilot studies on healthy volunteers was 5 gm in 100 ml boiled water twice daily, and the average human body weight is 70 kg; using the stock solution at the level of 5 gm/100 ml this dose is equal to 0.14 gm/kg body weight.

Acute toxicity study results: Rats and mice could tolerate the extract equivalent to 5 g/kg with no mortalities.

Sub Chronic and Chronic Toxicity Studies

These studies were carried out in rats and dogs. The experimental sub chronic dose used was 3 gm/kg body weight.

RATS: Three groups each of 10 mature male albino rats (160-185 g) were used. The drug was given by stomach tube twice daily for a period of 3 months at two dose levels 1.5 and experimental sub chronic dose (the drug was given as a water extract, but the dose is calculated as g/kg body weight).

Meanwhile, rats of the control group were given only the water as the vehicle. The rats were fed with standard feed and provided with water ad libitum. During the experiment all animals were observed daily for general conditions, and behavior. Body weight and food consumption in rats were recorded at week intervals.

After 2 weeks, 1 month and 3 months from drug administration, hematological (RBCS, WBCS, PCV, HB, phagocytosis and phagocytic index) and serum analysis for liver and renal functions [total protein, albumin, globulin, alanine aminotransferase (ALT), aspartate aminotransferase (AST), gamma glutamyl tansferase (GGT), alkaline phosphatase (ALP), urea, creatinine, glucose, triglycerides, total lipids and total cholesterol and alphafetoprotein] using commercial kits.

Kits for all biochemical studies were obtained from BIO-SYSTEMS® S.A. Costa Brava 30, Barcelona (Spain), while alpha-fetoprotein kit was obtained from ACON LABORATORIES®, INC. 4-108 Sorrento Valley Boulevard San Diego, Calif. 92121 USA.

At the end of the experiment (after 3 months), animals were weighed and anesthetized with ether for blood collection. Gross pathologic changes, weights of several organs and histological findings were recorded.

DOGS: Two groups each of 3 mature mongrel male dogs (7-11 kg) were used. The drug was added to the drinking water at the level of experimental sub chronic dose. Meanwhile, dogs of the control group were given only the vehicle. After 3 months from drug administration hematological and serum analysis were done as in rats.

Sub chronic and chronic toxicity study results: Daily administration of Eu2010-12 by gavage twice daily at doses of 1.5 or experimental sub chronic dose in rats, and its addition to the drinking water of dogs 3 g/kg for 3 months revealed no significant changes on the body weights, heart rates, and other physiological parameters and revealed no histological alterations in different organs. The following results were obtained:

1: Eu2010-12 did not induce any significant adverse changes in blood hematological parameters in rats and dogs (Tables 1, 2, 14). Nevertheless, the phagocytic activity at all periods after drug administration was significantly increased (Table 7).

2: Eu2010-12 induced a significant increase in total proteins and globulins in rats (Table 3), yet it did not exceed the normal reference range in all animals.

3: Eu2010-12 did not induce any abnormal liver and kidney functional changes as demonstrated by serum biochemical analysis in rats and dogs. Interestingly, Eu2010-12 induced a significant decrease in ALP, urea & creatinine in rats (Tables 3, 4, 5, 13, 16, 17). This suggests that this extract enhance the kidney function of the treated animal, consistent with its use for the treatment of UTIs in traditional folk medicine.

4: Although no significant change in blood glucose level was observed in animals receiving Eu2010-12 at the level of 1.5 gm/kg, significant decrease in blood glucose level occurred in animals receiving 3 gm/kg (Table 2).

5: Eu2010-12 induced a significant decrease in cholesterol, triglycerides and total lipids after its oral administration for 3 months in rats (Tables 2, 6).

6: Light Microscopic examination of the different organs in rats and mice revealed no significant alterations as compared to the control animals (data not shown).

Reproductive Studies

A fertility study was carried out in 80 male and female albino rats. The drug was given at the dose of experimental sub chronic dose (Rfd, which is 10% of the animal life span that is 90 days) twice daily to males and females, for respectively 35 and 14 days prior to mating. Dosed males and females were mated with non-dosed counterparts.

Dosed female rats were further treated throughout the gestation period. Control rats received the vehicle only. On day 20 of pregnancy the female rats were sacrificed and fetuses were delivered by caesarean section for further examination.

Another study tested embryotoxicity and teratogenicity. This study was carried out in female animals (20 rats, 40 mice, and 16 New Zealand rabbits). Animal groups were divided equally receiving the tested drug at doses of 0 and experimental sub chronic dose respectively twice daily.

Rats: Two groups of 10 female rats each received the tested drug at doses of 0 and experimental sub chronic dose twice daily from day 6 to day 15 of pregnancy. Rats were sacrificed on day 20 of pregnancy. Fetuses were delivered by caesarean section. Fetal skeleton and visceral organs were examined.

Mice: Two groups of 20 female mice each, received the tested drug at doses of 0 and experimental sub chronic dose twice daily from day 6 to day 15 of pregnancy. Mice were sacrificed on day 18 of pregnancy. Fetuses were delivered by caesarean section. Fetal skeleton and visceral organs were examined.

Rabbits: Two groups of 8 female New Zealand rabbits each received the tested drug at doses of 0 and experimental sub chronic dose twice daily from day 7 to day 19 of pregnancy. Rabbits were sacrificed on day 29 of pregnancy. Fetuses were delivered by caesarean section. Fetal skeleton and visceral organs were examined.

Peri- and post-natal studies were also performed. In the peri- and postnatal study, 10 pregnant rats received the drug at the doses of 0 and the experimental sub chronic dose twice daily. Dosing was started from day 16 of gestation and continued throughout the 3-week-lactation period. Ten other pregnant rats were used as controls. Observations on the offspring were made at birth and at day 4, 14 and 21 days after birth.

Eu2010-12 did not affect fertility. Dosed males showed comparable data with the controls when dosed at experimental sub chronic dose (Table 8). Eu2010-12 did not cause any embryotoxic or teratogenic effect (Tables 8, 9, 10, 11). Likewise, it did not cause any deleterious effects on the dosed females and their offspring. Litter size, survival rate and weight gain were comparable between groups (Table 9).

These fertility studies confirmed that Eu2010-12 showed no evidence of impaired fertility, teratogenic or embryotoxic effects at higher doses up to several times the recommended therapeutic dose of 10 gms daily (infusions or teas of 2 sachets daily), recomended by the PI based on previous pilot studies on healthy volunteers that were performed on the basis of the safety of this edible herb.

Mutagenicity and Cracinogenicity Studies

The mutagenic potential of the tested drug was evaluated by analysis of mitotic index, chromosomal aberrations and micronucleus technique. Twenty male and female mice were equally divided into two groups received the drug twice daily for 3 months at doses 0 and experimental sub chronic dose.

Analysis of chromosomal aberrations was done on femur bone marrow. The animals were sacrificed 1-2 hr after injection with colchicine (4 mg/kg body weight). Bone marrow preparation was made by extraction of bone marrow cell with 5-7 ml of KCl (0.65%) as a hypotonic solution at 37° C. for 25 min. The cells were centrifuged for 5 min at 1000 rpm and then fixed in methyl acetic acid (Carnoy) 3:1, then centrifuged at 1000 rpm for 5 min. The supernatant was discarded, the pellets resuspended in 5 ml of fixative and centrifugation repeated. This procedure was repeated twice. The cells spread into clean slides and stained with Giemsa.

The bone marrow was flushed out with 1-1.5 ml fetal calf serum and centrifuged at 1000 rpm for 5 min. The sediment cells were then smeared onto clean slides (3 for each animal). After drying, the slides were fixed in absolute methyl alcohol for 10 minutes and stained with 10% Giemsa stain.

Animals subjected to carcinogenic studies were divided into 4 equal groups receiving Eu2010-12 daily in the form of powder by its addition to their diets at different concentrations described in the methodology.

The carcinogenic potential of Eu2010-12 was investigated in rats and dogs by determination of alpha fetoprotein. Histological examination for carcinogenic activity was carried in mice. For further investigating the carcinogenic activity of the tested material in parenchymatous organs, eighty mice were equally divided into 4 groups and received the drug in the diet daily at the following levels 0, 0.25, 0.5 and 1% w/w respectively. Mice will be investigated after 6 and 12 months from the beginning of the experiment.

Statistical Analysis: The data were analyzed by ANOVA and mean values of various treatments were compared with control values. Results are presented as mean±S.E. and considered statistical significant if $p<0.05$.

Eu2010-12 did not induce any significant changes in chromosomal aberrations (fragment, deletion, ring and gap) and micronuclei after daily administration for 3 months in mice (Tables 11 and 12). The carcinogenic potential of Eu2010-12 was investigated in rats and dogs after 3 months by qualitative determination of alpha fetoprotein in their serum. All results in this category were negative in all animal species. Further studies are under investigation and will continue until one year in mice as previously mentioned.

The mutagenicity and carcinogenicity studies confirmed that Eu2010-12 had no evidence of mutagenic potentials or carcinogenic activity at higher doses up to several times the recommended therapeutic dose of 10 gms/70kg human body weight daily (infusions or teas of 2 sachets daily).

In summary, the extract has been shown to be safe at levels up to 1 g/kg in four species.

Animal NAFL Efficacy Studies

The present efficacy studies were conducted on 40 adult male albino rats weighing 120-150 grams. All animals were reared under the same environmental conditions regarding caging, light and temperature. The rats were fed standard rat diet and were allowed water ad libitum all through the experimental period (20 days).

Rats were divided into 2 main groups:

Group I (control group): Included 16 rats and were subdivided into 2 equal subgroups Subgroup Ia: 8 rats, served as normal control group, fed standard rat diet and allowed water ad libitum.

Subgroup Ib: 8 rats, served as experimental control group, fed standard rat diet and received Eu2010-12 in a dose of 8.5 mg/kg bw daily for 20 days.

Group II (experimental group): Included 24 rats. This group was subdivided into three equal subgroups.

Subgroup IIa (fatty liver induction group): 8 rats, received a single oral induction dose of acetaminophen on day 10 from the starting day in a dose of 500 mg/kg bw by oral gavage.

Subgroup IIb (prevention subgroup): 8 rats, received Eu2010-12 in a dose of 8.5 mg/kg bw daily for 10 days prior to induction with a single oral dose of 500 mg/kg bw of acetaminophen by oral gavage then sacrificed on the following day after induction.

Subgroup IIc (treatment subgroup): 8 rats, were kept at control conditions for 9 days, then received a single oral induction dose of acetaminophen on day 10 from the starting day in a dose of 500 mg/kg bw by oral gavage. The next days the rats received Eu2010-12 in a dose of 8.5 mg/kg bw daily for 10 days.

After the end of the experimental period all animals were sacrificed by decapitation. The abdomen was opened and specimens from the livers were taken and fixed in 10% formol saline and processed to get 10 micron paraffin sections for light microscopic examination using hematoxylin and eosin staining.

Group Ia: (control group): Liver specimens of this group revealed normal hepatic parenchyma with cords of hepatocytes radiating from the central veins. The hepatic cells appeared polyhedral in shape with well-defined boundaries and acidophilic cytoplasm. Each cell showed rounded vesicular and centrally located nucleus. Some binucleated cells were present. Hepatic sinusoids appeared as narrow spaces lined by endothelial and kupffer cells. The portal tracts showed normal duct radicals and blood vessels (data not shown).

Group Ib: (animals receiving 8.5 mg/kg bw): Light microscopic examination of liver specimens of these animals showed preservation of the hepatic architecture. Hepatocytes structure appeared nearly similar to that of the control subgroup.

Group II: (fatty liver induction group): Subgroup IIa: Liver of rats of this group showed variable degrees of hepatic affection. Many hepatocytes appeared swollen with moderate to severe cytoplasmic vacuolation and deeply stained shrunken nuclei. The cytoplasm of some cells showed increased acidophilia. Central veins were occasionally congested. Sinusoids were either dilated or obliterated. Increase in the number of Kupffer cells were noticed. Therefore, the acetaminophen induced nonalcholic fatty acid liver disease.

Group II: (fatty liver induction group): Subgroup IIb (preventive group): Rat liver of this group showed more or less normal hepatic structure and architecture with no cytoplasmic vacuolation of the liver cells. Therefore, the crude broomrape extract shows preventive effect in this induced nonalcoholic fatty liver animal model.

Group II: (fatty liver induction group): Subgroup IIc (receiving Eu2010-12 after induction): Liver of rats of this subgroup depicted nearly normal hepatic light microscopic appearance except for occasional dilatation of few sinusoids. Therefore, the crude broomrape extract shows treatment efficacy in this induced nonalcoholic fatty liver animal model.

In-Vitro Anti-HCV Screening

Peripheral blood mononuclear cells (PBMC) were prepared and then infected with 2-5% HCV-infected serum in RPMI culture medium containing 5-10% FBS. Different concentrations (10, 25, 50, 100, 250, 500 µg/ml) of the crude water extract of wild plant Eu2010-12 were added. Positive and negative control cultures were included. After 48-96 h of incubation at 37° C., 5% $CO_2$, and 95% humidity followed by total RNA extraction. The positive strand were detected by RT-PCR using HCV specific primers to the 5'-untranslated region of the virus.

Afterward, HPLC fractionation was performed of the crude water extract of the wild plant Eu2010-12 resulting in 10 fractions, 100-200 µg/ml of each of these fractions. Both the total lyophilized extract and the fractions were examined for anti-HCV activity.

Two fractions out of the 10 HPLC fractions showed ability to prevent cultured HCV replication in the in vitro test. Based on the results, it was concluded that the total extract prevented the replication of the HCV in vitro. In addition, 2 fractions showed promising inhibition of the hepatitis C virus progeny.

RT-PCR of HCV RNA

Total RNA was extracted from PBMC HCV-infected cells. Briefly, culture cells were mixed with 10-15 times volume of 4M guanidinium isothiocyanate containing 25 mM sodium citrate, 0.5% sarcosyl, 0.1 M β-mercaptoethanol, and 100 μL sodium acetate. The lysed cells were mixed with an equal volume of phenol, chloroform and isoamyl alcohol (25:24:1, pH 4). After vortexing of the sample, the mixture was centrifuged at 12-14 K rpm for 10-15 min at 4-8° C. The aqueous layer was collected and mixed with an equal volume of isopropanol. After incubation at −20° C. overnight, RNA was precipitated by centrifugation at 12-14 K rpm for 30-45 min at 4-8° C. and the precipitated RNA was washed twice with 70-80% ethanol.

The complimentary DNA (cDNA) and the first PCR reaction of the nested PCR detection system for the HCV RNA was performed in a 25-50 μL volume single-step reaction using the Ready-To-Go RT-PCR beads (AMERSHAM PHARMACIA BIOTECH®, Piscataway, N.J., USA), 2.5-10 μM from each of the RT downstream primer, PCR forward primer P1 and reverse primer P2. See El-Hawash S A, Abdel Wahab A E, El-Demellawy M A (2006). Cyanoacetic Acid Hydrazones of 3-(and 4-) Acetylpyridine and Some Derived Ring Systems as Potential Anti-tumor and Anti-HCV Agents. Arch Pharm (Weinheim) 339:14-23.

The thermal cycling protocol was as follows: 30-45 min at 42° C. for cDNA synthesis followed by 5 min at 95° C. and 30-35 cycles of 30 sec-1 min at 94° C., 30 sec-1 min at 55° C. and 30 sec-1 min at 72° C. The nested PCR amplification was performed in 25-50 μL reaction mixture containing 0.15-0.2 mM from each dNTP, 2.5-10 μM from each of the reverse nested primer and the forward nested primer, 1-2 units of Taq DNA polymerase (PROMEGA®, Madison, Wis., USA) and 5-10 μL from the RT-PCR reaction product in a 1×buffer supplied by the vendor. A fragment of 174 by length was identified in positive samples.

Crude water extract of wild plant Eu2010-12 was capable of preventing viral replication completely at concentration range from 250-500 μg/ml, while concentrations ranging from 10-100 μg/ml showed variable degree of viral replication prevention. At 10 μg/ml, the drug partially prevented viral replication.

In-Vitro Anti-HCV Screening

The same concentrations of the crude water extract of wild plant Eu2010-12 were examined for anti-HCV activity quantitatively using same culture system used for the qualitative test and using the ANALYTIK JENA AG HCV viral RNA extraction kit and the ROBOGEN HCV quantitative kit (BOMETERA, Germany).

Quantitative results were shown to be in agreement with previously qualitative results.

| Drug concentration (μg/ml) | HCV Viral Load (IU/ml) |
|---|---|
| Positive control | $1.28 \times 10^9$ |
| 500 | Zero |
| 250 | Zero |
| 100 | 144 |
| 50 | 388 |
| 10 | 461 |

In summary, the extract has been shown to be safe at levels up to 1 g/kg in four species, and has been shown to have efficacy against HCV in PBMCs, and showed preventative and treatment efficacy in induced nonalcoholic fatty liver animal models.

The current studies used whole plant, but future studies will be undertaken in order to determine which part of the plant has the most active ingredient and at which stage of the life cycle. Peripheral blood mononuclear cells (PBMC) can be assayed as above for these tests. Samples will be collected at various stages of the life cycle, details carefully noted and roots, stem, seed and the like each assayed for activity in the PBMC HCV assay.

In addition, fractionation and active ingredient characterization efforts will continue to identify which ingredient(s) are responsible for the efficacy of this herb.

The complete results are presented in the following tables.

TABLE 1

Hematological parameters of tats given (Eu2010-12) by gavage twice daily for 3 months.

| | Parameters | | |
|---|---|---|---|
| Drug | Hb (g/dl) | PCV % | RBCS ×10⁶/Cmm |
| Vehicle (10 ml dist. Water/kg) | | | |
| Pretreatment | 11.9 ± 0.32 | 40.0 ± 0.61 | 6.02 ± 0.25 |
| $2^{nd}$ week | 11.6 ± 0.40 | 40.2 ± 0.60 | 6.15 ± 0.21 |
| $1^{st}$ month | 12.0 ± 0.68 | 40.4 ± 1.41 | 6.2 ± 0.36 |
| $3^{rd}$ month | 11.8 ± 0.56 | 40.8 ± 1.31 | 6.28 ± 0.44 |
| 1.5 g/Kg | | | |
| Pretreatment | 11.8 ± 0.64 | 39.6 ± 0.72 | 6.3 ± 0.43 |
| $2^{nd}$ week | 12.0 ± 0.56 | 40.0 ± 1.36 | 5.88 ± 0.34 |
| $1^{st}$ month | 12.2 ± 0.56 | 41.0 ± 2.0 | 5.9 ± 0.33 |
| $3^{rd}$ month | 11.4 ± 0.57 | 41.6 ± 2.39 | 6.4 ± 0.25 |
| 3 g/kg | | | |
| Pretreatment | 11.6 ± 0.38 | 39.6 ± 1.12 | 6.2 ± 0.37 |
| $2^{nd}$ week | 12.2.064 | 40.1 ± 1.15 | 6.3 ± 0.54 |
| $1^{st}$ month | 11.5 ± 0.52 | 40.0 ± 1.05 | 5.86 ± 0.36 |
| $3^{rd}$ month | 11.8 ± 0.88 | 39.2 ± 0.9 | 6.3 ± 0.27 |

Values are mean ± S.E. N = 6 animals

TABLE 2

Hematological and biochemical parameters of tats given (Eu2010-12) by gavage twice daily for 3 months.

| | Parameters | | |
|---|---|---|---|
| Drug | WBCS ×10³/Cmm | Glucose (mg/dl) | Cholesterol (mg/dl) |
| Vehicle (10 ml dist. Water/kg) | | | |
| Pretreatment | 7.1 ± 0.24 | 66.6 ± 2.09 | 59.6 ± 1.29 |
| $2^{nd}$ week | 7.2 ± 0.31 | 65.2 ± 1.16 | 59.8 ± 1.59 |
| $1^{st}$ month | 6.92 ± 0.49 | 66.2 ± 1.93 | 60.6 ± 1.29 |
| $3^{rd}$ month | 6.8 ± 0.37 | 63.0 ± 3.04 | 56.8 ± 2.78 |
| 1.5 g/Kg | | | |
| Pretreatment | 6.60 ± 0.40 | 62.6 ± 2.36 | 61.4 ± 2.75 |
| $2^{nd}$ week | 6.80 ± 0.50 | 59.0 ± 2.12 | 57.4 ± 1.89 |
| $1^{st}$ month | 7.00 ± 0.44 | 58.8 ± 2.25 | 51.8 ± 1.07* |
| $3^{rd}$ month | 6.6 ± 0.51 | 57.6.62 | 49.2 ± 1.07* |
| 3 g/Kg | | | |
| Pretreatment | 6.9 ± 0.64 | 64.4 ± 2.02 | 60.8 ± 1.65 |
| $2^{nd}$ week | 7.1 ± 0.45 | 56.4 ± 2.06* | 53.8 ± 2.54 |
| $1^{st}$ month | 6.8 ± 0.37 | 57.2 ± 2.96* | 51.0 ± 1.52* |
| $3^{rd}$ month | 6.4 ± 0.51 | 55.6 ± 2.38* | 49.6 ± 1.03* |

Values are mean ± S.E. N = 6 animals
*Significantly different compared to control (pretreated group), P < 0.05.

TABLE 3

Serum protein profile of rats given (Eu2010-12) by gavage twice daily for 3 months.

| Drug | Protein (g/dl) | Albumin (g/dl) | Globulin (g/dl) |
|---|---|---|---|
| Vehicle (10 ml dist. Water/kg) | | | |
| Pretreatment | 5.08 ± 0.24 | 3.26 ± 0.27 | 1.82 ± 0.15 |
| $2^{nd}$ week | 5.12 ± 0.12 | 3.2 ± 0.14 | 1.92 ± 0.08 |
| $1^{st}$ month | 5.2 ± 0.22 | 3.28 ± 0.18 | 1.92 ± 0.08 |
| $3^{rd}$ month | 5.28 ± 0.21 | 3.5 ± 0.22 | 1.78 ± 0.19 |
| 1.5 g/Kg | | | |
| Pretreatment | 2.24 ± 0.22 | 3.34 ± 0.25 | 1.9 ± 0.07 |
| $2^{nd}$ week | 5.64 ± 0.27 | 3.66 ± 0.29 | 1.98 ± 0.02 |
| $1^{st}$ month | 5.48 ± 0.33 | 3.24 ± 0.44 | 2.24 ± 0.24* |
| $3^{rd}$ month | 5.48 ± 0.21 | 2.88 ± 0.41 | 2.6 ± 0.24* |
| 3 g/kg | | | |
| Pretreatment | 5.22 ± 0.21 | 3.36 ± 0.27 | 1.86 ± 0.15 |
| $2^{nd}$ week | 5.52 ± 0.26 | 3.34 ± 0.23 | 2.18 ± 0.22 |
| $1^{st}$ month | 6.0 ± 0.27* | 3.0 ± 0.27 | 3.0 ± 0.31* |
| $3^{rd}$ month | 5.7 ± 0.37* | 3.0 ± 0.31 | 2.7 ± 0.20* |

Values are mean ± S.E. N = 6 animals
*Significantly different compared to control (pretreated group), P < 0.05.

TABLE 4

Effect of administration of (Eu2010-12) twice daily for 3 months serum AST, ALT, and ALP in rats.

| Drug | Protein (g/dl) | Albumin (g/dl) | Globulin (g/dl) |
|---|---|---|---|
| Vehicle (10 ml dist. Water/kg) | | | |
| Pretreatment | 50.2 ± 1.56 | 17.2 ± 0.58 | 81.4 ± 1.12 |
| $2^{nd}$ week | 49.4 ± 2.36 | 16.6 ± 0.98 | 83.0 ± 1.52 |
| $1^{st}$ month | 47.8 ± 2.71 | 16.6 ± 0.92 | 82.4 ± 1.60 |
| $3^{rd}$ month | 46.8 ± 2.01 | 16.6 ± 0.46 | 81.2 ± 185 |
| 1.5 g/Kg | | | |
| Pretreatment | 48.8 ± 2.82 | 19.0 ± 0.71 | 82.2 ± 1.96 |
| $2^{nd}$ week | 48.0 ± 0.44 | 18.0 ± 0.71 | 80.6 ± 2.16 |
| $1^{st}$ month | 46.4 ± 2.71 | 17.4 ± 0.68 | 76.2 ± 2.44 |
| $3^{rd}$ month | 45.0 ± 2.10 | 16.8 ± 1.16 | 73.6 ± 2.73* |
| 3 g/kg | | | |
| Pretreatment | 47.6 ± 3.21 | 18.6 ± 0.51 | 79.8 ± 1.99 |
| $2^{nd}$ week | 45.6 ± 3.06 | 17.4 ± 0.60 | 79.2 ± 1.46 |
| $1^{st}$ month | 44.6 ± 2.93 | 16.0 ± 0.71* | 74.4 ± 2.32 |
| $3^{rd}$ month | 44.6 ± 2.93 | 16.0 ± 0.71* | 71.6 ± 2.91* |

Values are mean ± S.E. N = 6 animals
*Significantly different compared to control (pretreated group), P < 0.05.

TABLE 5

Effect of administration of (Eu2010-12) twice daily for 3 months serum GGT, urea and creatinine in rats.

| Drug | GGT (U/L) | Urea (mg/dl) | Creatinine (mg/dl) |
|---|---|---|---|
| Vehicle (10 ml dist. Water/kg) | | | |
| Pretreatment | 12.0 ± 0.71 | 19.2 ± 0.67 | 0.56 ± 0.05 |
| $2^{nd}$ week | 11.8 ± 0.86 | 19.8 ± 1.07 | 0.58 ± 0.07 |
| $1^{st}$ month | 11.2 ± 1.16 | 19.4 ± 1.75 | 0.56 ± 0.05 |
| $3^{rd}$ month | 12.5 ± 1.07 | 18.6 ± 2.07 | 0.58 ± 0.06 |
| 1.5 g/Kg | | | |
| Pretreatment | 12.4 ± 1.03 | 20.6 ± 0.93 | 0.60 ± 0.05 |
| $2^{nd}$ week | 12.2 ± 0.73 | 19.0 ± 0.89 | 0.58 ± 0.03 |
| $1^{st}$ month | 12.2 ± 0.80 | 19.0 ± 1.23 | 0.48 ± 0.03 |
| $3^{rd}$ month | 11.4 ± 0.98 | 17.2 ± 1.07 | 0.58 ± 0.03 |
| 3 g/kg | | | |
| Pretreatment | 12.8 ± 0.97 | 17.8 ± 1.28 | 0.6 ± 0.07 |
| $2^{nd}$ week | 12.6 ± 0.81 | 17.6 ± 2.32 | 0.58 ± 0.08 |
| $1^{st}$ month | 12.2 ± 1.24 | 16.2 ± 1.8 | 0.58 ± 0.8 |
| $3^{rd}$ month | 11.0 ± 0.98 | 15.6 ± 0.93* | 0.40 ± 0.04* |

Values are mean ± S.E. N = 6 animals
*Significantly different compared to control (pretreated group), P < 0.05.

TABLE 6

Effect of administration of (Eu2010-12) twice daily for 3 months serum Triglycerides and Total lipids in rats.

| Drug | Triglycerides (mg/dl) | Total Lipids (g/l) |
|---|---|---|
| Vehicle | | |
| Pretreatment | 104.4 ± 3.14 | 5.06 ± 0.40 |
| $2^{nd}$ week | 100.8 ± 5.13 | 5.1 ± 0.39 |
| $1^{st}$ month | 100.0 ± 7.26 | 5.0 ± 0.47 |
| $3^{rd}$ month | 101.0 ± 6.8 | 5.06 ± 0.37 |
| 1.5 g/Kg | | |
| Pretreatment | 104.0 ± 8.74 | 5.02 ± 0.34 |
| $2^{nd}$ week | 98.8 ± 7.12 | 4.88 ± 0.39 |
| $1^{st}$ month | 95.4 ± 7.24 | 3.84 ± 0.25* |
| $3^{rd}$ month | 91.6 ± 4.31 | 3.7 ± 0.43* |
| 3 g/kg | | |
| Pretreatment | 105.0 ± 7.26 | 4.78 ± 0.51 |
| $2^{nd}$ week | 99.0 ± 6.98 | 4.5 ± 0.31 |
| $1^{st}$ month | 94.0 ± 5.8* | 3.74 ± 0.23* |
| $3^{rd}$ month | 81.0 ± 3.68* | 3.54 ± 0.41* |

Values are mean ± S.E. N = 6 animals
*Significantly different compared to control (pretreated group), P < 0.05.

TABLE 7

Effect of administration of (Eu2010-12) by gavage twice daily for 3 months on phagocytic activity and phagocytic index in rats.

| Drug | phagocytic activity | phagocytic index |
|---|---|---|
| Vehicle (10 ml dist. Water/kg) | | |
| Pretreatment | 22.0 ± 0.71 | 1.86 ± 0.09 |
| $2^{nd}$ week | 23.4 ± 0.40 | 1.72 ± 0.03 |
| $1^{st}$ month | 23.2 ± 0.49 | 1.82 ± 0.11 |
| $3^{rd}$ month | 22.1 ± 0.50 | 1.75 ± 0.20 |
| 1.5 g/Kg | | |
| Pretreatment | 21.0 ± 0.63 | 1.78 ± 0.03 |
| $2^{nd}$ week | 24.4 ± 0.51* | 1.90 ± 0.10 |
| $1^{st}$ month | 25.0 ± 0.63* | 2.04 ± 0.06 |

TABLE 7-continued

Effect of administration of (Eu2010-12) by gavage twice daily for 3 months on phagocytic activity and phagocytic index in rats.

| Drug | Parameters | |
|---|---|---|
| | phagocytic activity | phagocytic index |
| 3rd month | 25.4 ± 0.60* | 2.10 ± 0.08 |
| 3 g/kg | | |
| Pretreatment | 22.0 ± 0.71 | 1.74 ± 0.05 |
| 2nd week | 25.8 ± 0.37* | 1.94 ± 0.09 |
| 1st month | 25.6 ± 0.51* | 1.86 ± 0.10 |
| 3rd month | 24.8 ± 0.14* | 1.88 ± 0.20 |

Values are mean ± S.E. N = 6 animals
*Significantly different compared to control (pretreated group), $P < 0.05$.

TABLE 8

Effect of administration of (Eu2010-12) given by gavage on the rats.

| | Dosage group (g/Kg) | | | |
|---|---|---|---|---|
| | 0 | | 3 | |
| | C-M + T-F | T-M + C-F | C-M + T-F | T-M + C-F |
| Adult rat data | | | | |
| No. of treated males n | 0 | 10 | 0 | 10 |
| No. of treated Females n | 10 | 0 | 10 | 0 |
| No. of pregnant rats n | 7 | 7 | 8 | 8 |
| No. of surviving Females n | 10 | 10 | 10 | 10 |
| Fertility index % | 70 | 70 | 80 | 80 |
| Litter data | | | | |
| Average no. of implantations m | 6.71 | 6.9 | 6.75 | 6.5 |
| No. of pregnancies | | | | |
| No. of alive fetuses % | 6.43 | 6.57 | 5.88 | 6.25 |
| No. of resorbed fetuses % | 4.17 | 4.05 | 3.7 | 3.84 |
| Average weight at birth (g) | 5.23 | 5.08 | 5.09 | 5.32 |
| Abnormalities % | — | — | — | — |

Values are mean ± S.E. N = 6 animals. C = Control M = Male T = Treated F = Female

TABLE 9

Effect of administration of (Eu2010-12) by gavage on the development and viability of first generation (F1) pups during the pre-weaning period on rats.

| | Dosage group (g/Kg) | |
|---|---|---|
| | 0 | 3 |
| Mean number of pups/Litter | | |
| Born | 6.2 ± 0.37 | 6.6 ± 0.51 |
| Born alive | 5.8 ± 0.30 | 6.2 ± 0.30 |
| Sex ratio (meals) | 49.4 ± 1.07 | 49.2 ± 1.02 |
| Mean pup weight (g) litter | | |
| Postnatal day O(PND) males | 5.14 ± 0.29 | 4.88 ± 0.33 |
| Females | 4.98 ± 0.06 | 4.84 ± 0.09 |
| PND 4 males | 7.92 ± 0.11 | |
| Females | 7.92 ± 0.11 | 7.74 ± 0.16 |
| PND 4 males | 7.62 ± 0.16 | 7.46 ± 0.31 |
| Females | 15.34 ± 0.55 | 15.7 ± 0.43 |
| PND 4 males | 14.5 ± 0.48 | 14.2 ± 0.73 |
| Females | 25.6 ± 0.75 | 26.0 ± 0.54 |
| PND 4 males | 23.8 ± 1.24 | 24.2 ± 1.24 |
| No. of pups alive on PND 0 | 100 | 100 |

TABLE 9-continued

Effect of administration of (Eu2010-12) by gavage on the development and viability of first generation (F1) pups during the pre-weaning period on rats.

| | Dosage group (g/Kg) | |
|---|---|---|
| | 0 | 3 |

Values are mean ± S.E. N = 6 animals.

TABLE 10

Reproductive parameters in mice given (Eu2010-12).

| | Dose | |
|---|---|---|
| | 0 | 3 g/Kg |
| No. bred | 20 | 20 |
| No. pregnant | 16 | 18 |
| No. aborted | 0 | 0 |
| No. litters totally resorbed | 0 | 0 |
| No. corpora lutea | 7.0 ± 0.25 | 7.2 ± 0.30 |
| No. implantation | 6.37 ± 0.23 | 6.17 ± 0.21 |
| Dead fetuses | 0 | 0 |
| Litter size | 6.0 ± 0.20 | 6.17 ± 0.22 |
| Mean fetal body weight (g) | 1.1 ± 0.02 | 1.06 ± 0.02 |
| Abnormalities % | 0 | 0 |

TABLE 11

Reproductive parameters in rabbits given (Eu2010-12)

| | Dose | |
|---|---|---|
| | 0 | 3 g/Kg |
| No. bred | 8 | 8 |
| No. pregnant | 6 | 6 |
| No. aborted | 0 | 0 |
| No. litters totally resorbed | 0 | 0 |
| No. corpora lutea | 7.83 ± 0.47 | 8.67 ± 0.49 |
| No. implantation | 6.67 ± 0.42 | 7.67 ± 0.40 |
| Dead fetuses | 0 | 0 |
| Litter size | 6.33 ± 0.40 | 7.5 ± 0.62 |
| Mean fetal body weight (g) | 36.0 ± 1.29 | 37.67 ± 1.48 |
| Abnormalities % | 0 | 0 |

TABLE 12

Different Kinds of chromosomal aberrations in mice treated with (Eu2010-12) by gavage twice daily for 3 months.

| Dosage group g/Kg | Parameter* | | | |
|---|---|---|---|---|
| | Fragment | Deletion | Ring | End to end association |
| 0 | 1.4 ± 0.2 | 0.6 ± 0.02 | 0 | 2.2 ± 0.3 |
| 3 | 1.2 ± 0.5 | 0.8 ± 0.03 | 0 | 1.8 ± 0.3 |

Values are mean ± S.E. N = 6 animals
*250 metaphases were examined per each treatment

TABLE 13

Micronucleus (MN) and mitotic index in mice treated with (Eu2010-12) by gavage twice daily for 3 months.

| Dosage group g/Kg | Mitotic index* | Parameter Micronucleus** (Nuclear budding) | Micronucleus** (Nuclear fragmentation) | End to end association |
|---|---|---|---|---|
| 0 | 9.2 ± 0.5 | 1.6 ± 0.24 | 0.8 ± 0.3 | 2.2 ± 0.3 |
| 3 | 8.4 ± 0.9 | 1.2 ± 0.49 | 0.8 ± 0.4 | 1.8 ± 0.3 |

Values are mean ± S.E. N = 6 animals [0001]
*No of dividing cells in 500 cells
**Micronucleus incidence in 500 polychromatic erythrocytes.

TABLE 14

Hematological parameters of dogs given (Eu2010-12) by gavage twice daily for 3 months.

| Dosage group | Hb (g/dl) | PCV % | RBCS ×10⁶ cmm | WBCS ×10³/cmm |
|---|---|---|---|---|
| Vehicle | | | | |
| Pretreatment | 13.0 ± 0.71 | 35.2 ± 1.02 | 5.82 ± 0.29 | 6.8 ± 0.51 |
| After 3 months | 12.5 ± 1.08 | 35.6 ± 1.6 | 6.06 ± 0.33 | 6.78 ± 0.50 |
| 3 g/Kg | | | | |
| Pretreatment | 12.6 ± 1.21 | 34.8 ± 1.5 | 6.0 ± 0.44 | 6.5 ± 0.50 |
| After 3 months | 12.4 ± 0.51 | 35.6 ± 1.84 | 6.16 ± 0.39 | 6.56 ± 0.41 |

Values are mean ± S.E. N = 6 animals [0001]

TABLE 15

Serum protein profile of dogs given (Eu2010-12) for 3 months.

| Drug | Protein (g/dl) | Albumin (g/dl) | Globulin (g/dl) |
|---|---|---|---|
| Vehicle | | | |
| Pretreatment | 6.0 ± 0.28 | 3.67 ± 0.33 | 2.33 ± 0.17 |
| After 3 months | 5.87 ± 0.21 | 3.70 ± 0.17 | 2.17 ± 0.09 |
| 3 g/Kg | | | |
| Pretreatment | 6.07 ± 0.19 | 4.23 ± 0.12 | 1.84 ± 0.26 |
| After 3 months | 6.23 ± 0.26 | 4.37 ± 0.29 | 1.86 ± 0.24 |

Values are mean ± S.E. N = 6 animals

TABLE 16

Effect of administration of (Eu2010-12) on serum AST, ALT, ALP and GGT in dogs.

| Drug | AST (U/L) | ALT (U/L) | ALP (U/L) | GGT (U/L) |
|---|---|---|---|---|
| Vehicle | | | | |
| Pretreatment | 22.4 ± 1.21 | 19.6 ± 0.51 | 77.0 ± 1.82 | 6.4 ± 0.51 |
| After 3 months | 21.8 ± 1.36 | 18.8 ± 1.16 | 78.4 ± 2.86 | 6.6 ± 0.68 |
| 3 g/Kg | | | | |
| Pretreatment | 21.4 ± 1.75 | 20.6 ± 1.29 | 74.2 ± 2.96 | 6.4 ± 0.51 |
| After 3 months | 20.4 ± 137 | 20.2 ± 1.66 | 73.8 ± 1.78 | 6.2 ± 0.58 |

Values are mean ± S.E. N = 6 animals

TABLE 17

Effect of administration of (Eu2010-12) on urea, creatinine and glucose in dogs.

| Drug | Urea (mg/dl) | Creatinine (mg/dl) | Glucose (mg/dl) |
|---|---|---|---|
| Vehicle | | | |
| Pretreatment | 19.8 ± 1.07 | 0.35 ± 0.03 | 65.2 ± 1.94 |
| After 3 months | 21.0 ± 1.00 | 0.36 ± 0.04 | 63.0 ± 2.40 |
| 3 g/Kg | | | |
| Pretreatment | 20.4 ± 0.68 | 0.34 ± 0.03 | 67.0 ± 2.03 |
| After 3 months | 19.6 ± 0.93 | 0.35 ± 0.04 | 64.4 ± 1.69 |

Values are mean ± S.E. N = 6 animals

The following references are incorporated by reference herein in their entireties for all purposes.

El-Hawash S A, Abdel Wahab A E, El-Demellawy M A (2006). Cyanoacetic Acid Hydrazones of 3-(and 4-) Acetylpyridine and Some Derived Ring Systems as Potential Anti-tumor and Anti-HCV Agents. Arch Pharm (Weinheim). 339:14-23.

What is claimed is:

1. A method of treating hepatitis C virus (HCV), comprising administering an effective amount of a composition comprising an aqueous extract of *Orobanche aegyptiaca* together with a pharmaceutically acceptable carrier to a patient with HCV, whereby the aqueous extract of said *Orobanche aegyptiaca* is prepared by powdering dried *Orobanche aegyptiaca*, extracting with water in an autoclave under pressure and collecting and lyophilizing the filtrate, wherein the filtrate is the aqueous extract of *Orobanche aegyptiaca*.

* * * * *